United States Patent
Brown et al.

(10) Patent No.: US 8,790,501 B2
(45) Date of Patent: Jul. 29, 2014

(54) SENSOR ASSEMBLIES AND VENT MEMBERS THEREFOR

(75) Inventors: Michael Alvin Brown, Cranberry Township, PA (US); Towner Bennett Scheffler, Butler, PA (US)

(73) Assignee: MSA Technology, LLC, Cranberry Township, PA (US)

( * ) Notice: Subject to any disclaimer, the term of this patent is extended or adjusted under 35 U.S.C. 154(b) by 29 days.

(21) Appl. No.: 12/914,929

(22) Filed: Oct. 28, 2010

(65) Prior Publication Data

US 2011/0100814 A1    May 5, 2011

Related U.S. Application Data

(60) Provisional application No. 61/256,712, filed on Oct. 30, 2009.

(51) Int. Cl.
*G01N 27/413* (2006.01)
*G01N 27/30* (2006.01)

(52) U.S. Cl.
CPC .................................. *G01N 27/304* (2013.01)
USPC ............ 204/412; 204/415; 204/400; 204/409

(58) Field of Classification Search
CPC .................................................... G01N 27/304
USPC ............... 204/412, 415, 431–432; 429/82–89
See application file for complete search history.

(56) References Cited

U.S. PATENT DOCUMENTS

| | | | |
|---|---|---|---|
| 4,147,841 A * | 4/1979 | Shroff | 429/86 |
| 4,406,770 A * | 9/1983 | Chan et al. | 204/406 |
| 4,822,474 A | 4/1989 | Corrado | |
| 4,916,034 A | 4/1990 | Hulsebus | |
| 5,284,566 A * | 2/1994 | Cuomo et al. | 204/412 |
| 5,624,546 A | 4/1997 | Milco | |
| 5,944,969 A | 8/1999 | Scheffler | |
| 6,641,949 B2 | 11/2003 | Cheiky | |
| 2005/0023153 A1* | 2/2005 | Bakker et al. | 205/775 |
| 2006/0124458 A1 | 6/2006 | Nauber | |

FOREIGN PATENT DOCUMENTS

WO  PCT/US2010/054582    10/2010

* cited by examiner

*Primary Examiner* — Bach Dinh
(74) *Attorney, Agent, or Firm* — Bartony & Associates, LLC

(57) ABSTRACT

A sensor includes a housing, at least two electrodes within the housing, an electrolyte providing ionic conductivity between the electrodes and a vent member including a first section including a portion extending through a passage in the housing. The vent member also includes at least one extending member connected to the first section that extends through at least a portion of an interior of the housing. The first section of the vent member is porous so that gas can diffuse from the interior of the housing to an exterior of the housing via the vent member.

21 Claims, 6 Drawing Sheets

SENSOR ASSEMBLIES AND VENT MEMBERS THEREFOR

CROSS-REFERENCE TO RELATED APPLICATION

This application claims benefit of U.S. Provisional Patent Application Ser. No. 61/256,712, the disclosure of which is incorporated herein by reference.

BACKGROUND

The terms used herein are not intended to be limited to any particular narrow interpretation unless clearly stated otherwise in this document. The disclosure of any references cited herein is incorporated by reference.

Amperometric electrochemical gas sensors are electrochemical cells similar in structure and operation to batteries and fuel cells. As such, these three devices have several structures in common, including, (i) an anode or anode compartment (wherein electrochemical oxidation occurs), (ii) a cathode, or cathode compartment (wherein electrochemical reduction occurs), (iii) an ionically conductive electrolyte (which maintains ionic electrical contact between the two electrodes, (iv) a housing (which encloses the electrodes and electrolyte), (v) contacts or poles (which are generally metallic electrical contacts between the electrodes and external circuitry) and (vi) external electronic circuitry used in connection with these devices. Batteries and fuel cells function primarily as power sources and place few design restrictions on the circuitry to which they may be placed in electrical contact. Amperometric gas sensors often require the use of specific driving circuitry (for example, a potentiostat) for proper function. There are, however, amperometric gas sensors that function analogously to fuel cells, and require only a method of measuring the electrical current which flows between the anode and cathode in the presence of the target or analyte gas.

Batteries are self-contained electrochemical energy storage and conversion devices. They are arranged so that both the anode and the cathode include, or are in intimate electrical contact with, relatively large quantities of substances with different electrochemical energies. Significant and useful amounts of electrical current flow through electronic circuitry when the anode and cathode poles of a battery are connected to the electronic circuitry. The source of this current is the electrochemical conversions of the anode and cathode materials (oxidation and reduction). Batteries are self-contained, from an electrochemical point of view, in that they are fabricated with sufficient anode material and cathode material to provide a useful lifetime or amount of electrical energy. As such, batteries are usually well sealed. In many designs, batteries are hermetically sealed. Common examples of batteries include the Leclanche cell (the "dry" cell) and the Plante cell (the lead acid battery).

Fuel cells, on the other hand, are electrochemical energy conversion devices that require an external supply of anode material, of cathode material, or of both anode material and cathode material. The electrodes of fuel cells are usually electrocatalytic in nature. In that regard, the fuel cell electrodes provide electrochemically active surfaces to support the electrochemical reactions of the cell, but do not actually chemically participate in the reactions. Unlike a battery, the useful life of which is generally over when the electrochemically active electrode materials are consumed, a fuel cell will operate continuously as long as electrochemically active fuel (anode material) and oxidizer (cathode material) are supplied to the device. An example of a common fuel cell is the Grove cell, or hydrogen-oxygen fuel cell. In the Grove cell, hydrogen is the fuel and oxygen is the oxidizer.

Amperometric electrochemical gas sensors are special cases of fuel cells. They are typically miniature in size (compared to fuel cells used for power generation) and are designed to use a target gas of analytical interest (that is, the analyte gas) as fuel. In the absence of the target gas, there are no bulk electrochemical conversions (Faradaic reactions) occurring at the electrodes, and thus, essentially zero current flows in the sensor. When present, the analyte gas undergoes electrochemical oxidation or reduction, resulting in the generation of Faradaic currents. The resultant current flow is sensed by the external driving circuitry and provides the analytical signal of the sensor. Typically, the observed current is directly proportional to the concentration of the analyte gas.

As discussed above, batteries, fuel cells and amperometric electrochemical gas sensors are similar in may respects. However, the manufacture of amperometric gas sensors poses several unique difficulties. First, unlike batteries, there must be a gas inlet to allow the analyte gas to enter the cell. There must also be contacts or poles which carry the current from the surfaces of the electrodes to external circuitry. Finally, the sensor must be fabricated in such a way as to retain the ionic electrolyte, which is often a highly corrosive aqueous acid or base. Sealing amperometric electrochemical gas sensors against leakage of the internal liquid electrolyte, while allowing entry of the analyte gas and collection of the resultant currents, are clearly important features of the mechanical design of electrochemical gas sensors.

Oxygen sensors are a special case of amperometric electrochemical gas sensors. Typically, electrochemical oxygen sensors include a noble metal working electrode and a sacrificial metal anode, which is typically lead or zinc. Sensors of this type have been used for many years to detect and measure oxygen concentrations in a variety of applications. Lead-based sensors suffer from several disadvantages, including a limited lifetime and the use of toxic metals.

Nonetheless, the sacrificial metal anode of oxygen sensors is typically a lead anode. Oxygen that enters the sensor is reduced at the working electrode, while the lead anode is oxidized to lead oxide. The sensor operates as long as there is electrochemically accessible lead in the sensor. To increase service lifetime, the lead content must be increased or the influx of oxygen must be decreased. Each of these paths to increasing sensor lifetime has associated advantages and disadvantages. In any event, however, the lifetime of the sensor is limited by the amount of lead present therein, which is determined at the time of manufacture.

Recently, a new type of oxygen sensor, typically referred to as "oxygen pump" sensors, have been disclosed. Oxygen pump sensors do not include a sacrificial base metal anode. Instead, oxygen pump sensors include an electrocatalytic anode or counter electrode. Oxygen entering the sensor is reduced to an oxide ion at the working electrode. Concurrently, the electrolyte is oxidized at the counter electrode, producing oxygen on a one-to-one molecular basis. Oxygen sensors of this type may have much longer useful service lifetimes than those that include a sacrificial anode. However, oxygen that is produced at the counter electrode needs to be removed to ensure the proper operation of an oxygen pump sensor. If oxygen is not removed in an efficient manner, internally produced oxygen can pressurize the sensor and find its way to the working electrode, thus affecting the analytical signal of the sensor. Additionally, an increase in internal pressure may cause the liquid electrolyte to leak from the internal portions of the sensor housing.

A variety of sensors that operate on the oxygen pump principle have been developed. Those sensors include a thin porous, hydrophobic membrane to create a vent system to vent generated oxygen. While these membrane-based vent systems can create diffusion paths to vent oxygen from the interior of the sensor housing, the sensor housing must include a passage or hole that is covered by the thin porous, hydrophobic membrane. Such holes or passages are associated with an increased risk of electrolyte leakage. Moreover, the efficient functioning or operation of a membrane-based vent system can be affected by the orientation of the sensor. For example, in certain orientations, the interior surface of the membrane may be completely wetted or contacted by liquid electrolyte, which can significantly adversely affect the operation of the membrane to vent gas. Providing more than one passage/membrane vent at different positions can reduce position- or orientation-dependent effects, but can increase the potential for leakage of liquid electrolyte from the sensor.

SUMMARY

In one aspect, a sensor includes a housing, at least two electrodes within the housing, an electrolyte providing ionic conductivity between the electrodes and a vent member. The vent member includes a first section including a portion extending through a passage in the housing, which is connected to the first section that extends through at least a portion of an interior of the housing. The first section of the vent member is porous so that gas can diffuse from the interior of the housing to an exterior of the housing via the vent member. The vent member can, for example, resist the flow of electrolyte therethrough.

In a number of embodiments, the vent member further includes a second section connected to the portion extending through the passage. The second section can, for example, be porous and can, for example, be attached to an exterior surface of the housing. The second section can, for example, extend beyond the perimeter of the passage to cover the passage. The second section can, for example, extend at an angle to the portion extending through the passage. In a number of embodiments, the second section extends generally perpendicularly to the portion extending through the passage.

The first section and the second section can, for example, be formed monolithically from individual particles of polymeric material to provide a gas diffusion pathway therethrough.

The extending member (as well as the portion extending through the passage and the second section) can, for example, be molded from individual particles of polymeric material. At least a portion of the individual particles can, for example, include or be formed of polytetrafluoroethylene.

In a number of embodiments, at least the extending member of the vent member is hydrophobic, oleophobic or multiphobic.

The extending member can, for example, extend through the interior of the housing so that a surface area of the extending member within the interior of the housing cannot be completely contacted by electrolyte.

The working electrode can, for example, be adapted to reduce oxygen to an oxide ion, and the sensor can, for example, be adapted to sense oxygen.

In another aspect, a method of venting gas from an interior of a sensor, which includes a housing, at least two electrodes within the housing and an electrolyte providing ionic conductivity between the electrodes, includes: providing a vent member including a first section including a portion extending through a passage in the housing and at least one extending member connected to the portion extending through the passage. The extending member extends at least partially through a portion of an interior of the housing, the first section being porous so that gas can diffuse from the interior of the housing to an exterior of the housing through the vent member.

In a further aspect, a container includes a housing and a vent member including a first section including a portion extending through a passage in the housing and connected to at least one extending member that extends through at least a portion of an interior of the housing. The first section is porous so that gas can diffuse from the interior of the housing to an exterior of the housing. The first section of the vent member can, for example, resist the flow of liquid therethrough.

The vent member can, for example, further include a second section in connection with the portion extending through the passage. The second section can, for example, be porous and can, for example, be attached to an exterior surface of the housing.

In a number of embodiments, the extending member extends through the interior of the housing so that a surface area of the extending member within the interior of the housing cannot be completely contacted by a liquid within the housing. The liquid can, for example, include an electrolyte. The second section can, for example, extend at an angle to the portion extending through the passage.

In several embodiments, the first section and the second section are formed monolithically from individual particles of polymeric material.

Vent members described herein reduce position- or orientation-dependency without increasing the potential for electrolyte leakage associated with forming multiple passages in a sensor (or other) housing to provide a robust and efficient system for venting gas (for example, oxygen) from the interior of a sensor (or other) housing.

The devices, systems and/or methods described herein, along with the attributes and attendant advantages thereof, will best be appreciated and understood in view of the following detailed description taken in conjunction with the accompanying drawings.

DETAILED DESCRIPTION

Figure 1A:
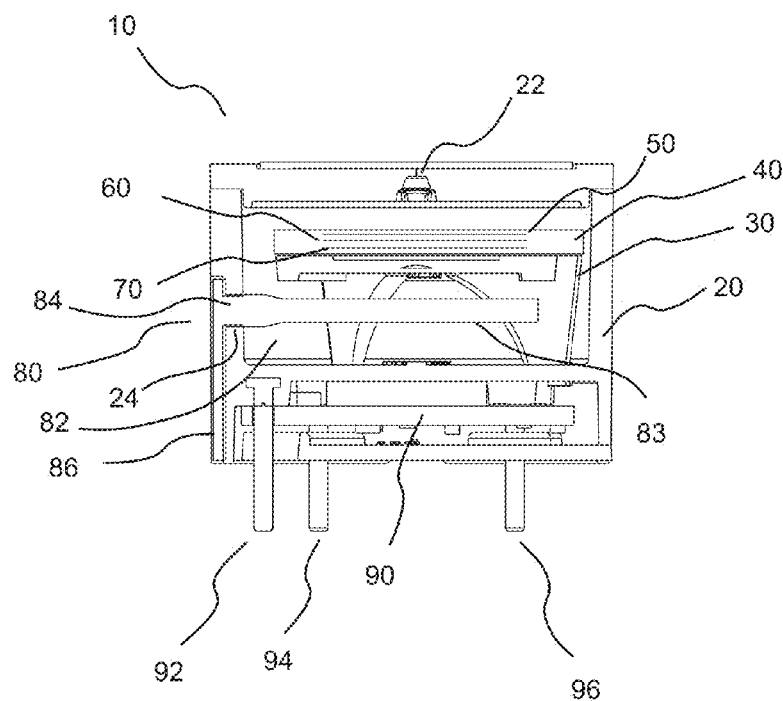
FIG. 1A illustrates a side, cutaway view of an embodiment of a sensor including a vent member.

As used herein and in the appended claims, the singular forms "a," "an", and "the" include plural references unless the context clearly dictates otherwise. Thus, for example, reference to "an extending member" includes a plurality of such extending members and equivalents thereof known to those skilled in the art, and so forth, and reference to "the extending member" is a reference to one or more such extending members and equivalents thereof known to those skilled in the art, and so forth.

In several embodiments, a vent member includes at least a first section including at least one three-dimensional member or structure which extends within a housing of, for example, a sensor to provide a vent path for one or more gases from within the housing to the exterior of the housing.

The extending member or members can be sized and shaped in any suitable manner. In several embodiments, the extending member extends through the housing in such a manner that the function of the extending member to provide a vent path for gas to exit the housing is not significantly affected by the position or orientation of the housing. In that regard, in several embodiments, the extending member extends through the housing so that the electrolyte does not wet or contact the surface of the extending member over the entire surface of that portion of the extending member within the housing regardless of the positioning or orientation of the sensor housing. In that regard, the extending member functions more efficiently to vent gas from the interior of the sensor housing if at least a portion of the extending member is in contact with a volume (for example, a bubble) of gas within the sensor housing. The extending member can, for example, extend in any direction through the housing in, for example, a generally linear and/or generally curvilinear manner.

The vent member can, for example, be fabricated separately from the housing and assembled therewith. The vent member can also function as part or a portion of the sensor housing.

The extending member can, for example, include or be formed from a porous polymeric or plastic material. In the case of an aqueous electrolyte, the porous polymer or other material of the extending member can be generally hydrophobic in nature to minimize or eliminate any flow of the aqueous electrolyte therethrough. In the case of a non-aqueous (for example, organic) electrolyte, the porous plastic or other material can be generally oleophobic in nature to minimize or eliminate any flow of the non-aqueous electrolyte therethrough. The porous plastic material can also be hydrophobic and oleophobic. Such materials are referred to as "multiphobic". The extending member can also be chemically or otherwise treated to minimize or eliminate liquid electrolyte flow or leakage therethrough.

In general, the term "hydrophobic" as used herein refers to materials that are substantially or completely resistant to wetting by water at pressures experienced within electrochemical sensors (and thus limit flow of aqueous electrolyte therethrough in the case of the extending member). In general, the term "oleophobic" as used herein refers to materials that are substantially or completely resistant to wetting by low-surface tension liquids such as non-aqueous electrolyte systems at pressures experienced within electrochemical sensors (and thus limit flow of non-aqueous electrolyte therethrough in the case of the extending member). As used herein, the phrase "low-surface tension liquids" refers generally to liquids having a surface tension less than that of water. Hydrophobic, oleophobic, and multiphobic materials are, for example, discussed in U.S. Pat. No. 5,944,969.

The material(s) (for example, porous plastic material) of the extending member are also preferably substantially chemically inert and thermally inert under the conditions in which electrochemical sensors are typically used.

In several embodiments, extending members were formed from porous PTFE (polytetrafluoroethylene). However, any polymeric or other material that provides the desired characteristics of, for example, porosity, hydrophobicity and/or oleophobicity can be used.

As described above, the extending member or members can take virtually any shape. Shapes studied have included rods of a circular or rectilinear cross-section. However, an extending member or members of generally any cross-sectional shape can be used. In several studies, the members or shapes were cut from pre-molded rods or from sheet stock. Complicated, three-dimensional shapes can, for example, be produced by a molding individual polymer particles into desired three-dimensional structure. In several embodiments, molded or sintered polymer structures were formed from polytetrafluoroethylene (PTFE) particles having particle sizes (diameters) in the range of 20-200 µm. In a number of embodiments, particles were screened or sifted to have a particle size/diameter less than 150 µm, less than 108 µm or less than 90 µm. The resulting three-dimensional structure had an effective pore size of 0.5 µm or less than 0.5 µm.

In the case of sintered polymer structures, polymer particles can, for example, be heated to a temperature above the glass transition temperature ($T_g$) but below the melt temperature ($T_m$). While heated above the glass transition temperature, the polymer particles adhere to each other. A controlled porosity is provided by the interstitial spacing or volume between particles. In a number of embodiments, pressure can be applied to the heated polymer particles to facilitate adherence and/or molding. Polymer particles can be sintered in a mold of virtually any shape to provide a desired three-dimensional element.

Alternatively, an open cell foam can be formed. In an open cell foam, pores are connected to form an interconnected porous network. For example, a polyurethane and/or polyurea foam can be formed during polymerization using a blowing agent such as water.

In a number of representative studies, vent members including porous extending members formed via sintering of PTFE particles were incorporated into sensor housings by a variety of methods including, for example, heat staking, ultrasonic welding, laser welding, adhesives, and injection molding. As is clear to those skilled in the art, other methodologies of attaching or incorporating the vent members into sensor housings are suitable. In all studies, vent members including three-dimensional, porous polymeric extending members provided efficient and effective gas diffusion paths while maintaining robustness of the sensor housing against electrolyte leakage.

Figure 1B:
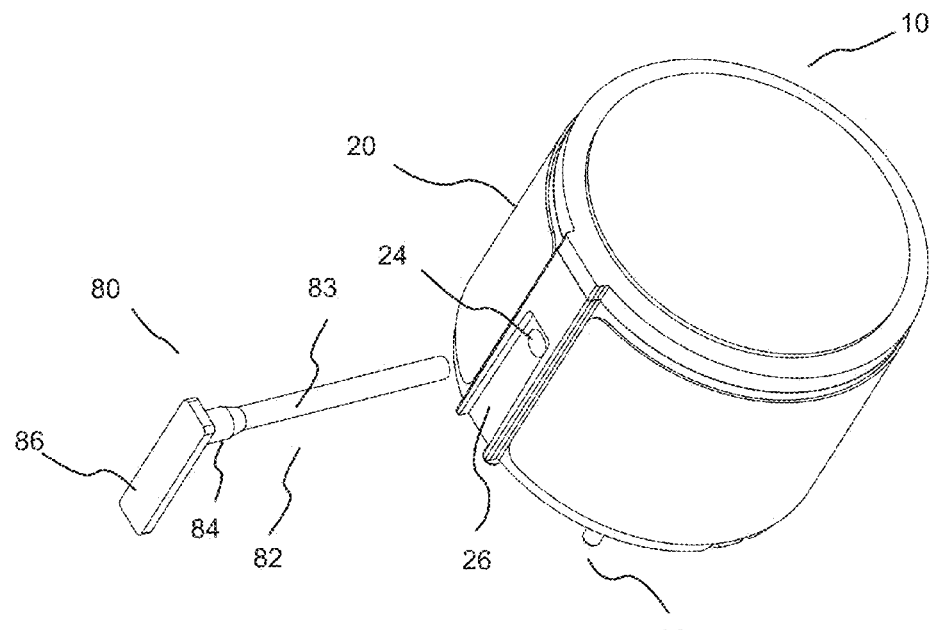
FIG. 1B illustrates a perspective view of the sensor of FIG. 1A wherein the vent member is separated from the sensor housing.
Figure 2:
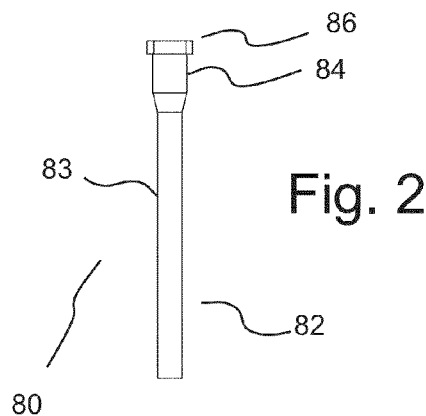
FIG. 2 illustrates a side view of the extending vent member of FIG. 1.
Figure 4:
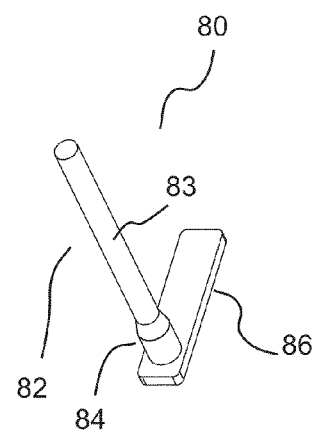
FIG. 4 illustrates a perspective view of the vent member of FIG. 1.
Figure 3:
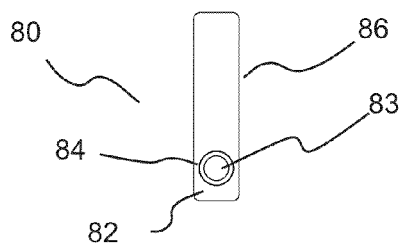
FIG. 3 illustrates a front view of the vent member of FIG. 1.

FIGS. 1A and 1B illustrate an embodiment of a sensor 10 including a housing 20. A sensor support member 30 is positioned within housing 20, which can, for example, provide support for at least two electrodes (for example, a working electrode and a counter electrode). Support member 30 can provide support for one or more other electrodes, including, for example, a reference electrode as known in the art. In general, a reference electrode is used to maintain the working electrode at a known voltage or potential. An analyte gas can enter housing 20 via an inlet passage 22.

An electrolyte can, for example, be at least partially absorbed upon wicking material 40 (illustrated schematically in FIG. 1A) as known in the sensor arts, which is supported by sensor support 30. The electrolyte provides ionic conductivity between electrodes 50, 60 and 70 (for example, a working or sensing electrode, a reference electrode and a counter electrode). Wicking material 40 also operates to physically separate electrodes 50, 60 and 70 to prevent short circuits therebetween. Sensor housing 20 includes a reserve volume, for example, below sensor support 30 (in the orientation of FIG. 1) to, for example, provide additional volume for the electrolyte should the volume of the electrolyte increase as a result of water absorption in the case of a hygroscopic electrolyte.

In the embodiment of FIGS. 1A and 1B, a vent member 80 includes a first section 82 including at least one extending member 83 that extends (that is, has a length to extend) through at least a portion of the interior volume of housing 20. As described above, first, extending member 83 can extend through housing 20 so that the surface area of extending member 83 cannot be entirely contacted by or wetted by the electrolyte. Thus, orientation- or position-independent gas venting is provided in the embodiment of FIGS. 1A and 1B (as well as other embodiments) with only a single passage (that is, passage 24) formed in housing 20 for gas venting. At least a portion of extending member 83 is thus maintained in contact with a volume of gas, which assists in maintaining efficient operation thereof to remove gas (for example, oxygen in the case of an oxygen pump type sensor). In several embodiments of an oxygen pump sensor, extending member 83 is positioned to provide an easier diffusion path from the counter electrode to extending member 83 than from the counter electrode to inlet passage 22.

Vent member 80 is also illustrated in FIGS. 2 through 5. In the illustrated embodiment, extending member 83 is generally cylindrical in shape. In the illustrated embodiment, first section 82 of vent member 80 also includes a portion 84 connected to extending member 83 that is adjacent to and extends through passage 24 when vent member 80 is in operative connection with housing 20. Portion 84 can, for example, be larger in diameter than extending member 83, and can be dimensioned to have a diameter slightly less than the diameter of passage 24. In a number of embodiments, first section 80 (including portion 84 and extending member 83) was formed monolithically.

In the illustrated embodiment, vent member 80 further includes a second section or member 86, which extends generally perpendicular to portion 84 of first section 80. Second section 86 can, for example, facilitate forming a suitable connection with an exterior of housing 20. In that regard, portion 84 of first section 80 extends through passage 24 in housing 20 as described above to connect to extending member or members 83. In the illustrated embodiment, second section 86 has a width greater than the diameter of portion 84 and covers passage 24 (extending beyond the diameter or perimeter of passage 24) to create a seal (to limit the potential for the escape of liquid electrolyte) and to provide surface area to ensure a secure engagement with or connection of vent member 80 with housing 20. Second section 86 can, for example, be attached to housing 20 via heat staking, ultrasonic welding, laser welding, adhesives, injection molding or via any other suitable manner of attachment. Whatever the method of attachment of vent member 80 to housing 20, care should be taken to not destroy the diffusion pathway provided by vent member 80 to vent gas from the interior of housing 20 to the exterior thereof. As illustrated in FIG. 1B, housing 20 can, for example, include a seating 26 dimensioned to receive and seat second member 84.

In the illustrated embodiment, second section 86 extends at an angle to portion 84 (perpendicular in the illustrated embodiment) to facilitate covering of passage 24 and to facilitate providing surface area to conform to and form a connection with a surface of housing 20. In the illustrated embodiment, second section 86 is formed as a generally rectangular flat ribbon of material. As described above, generally flat second section 86 facilitates connection with housing 20.

Figure 6:
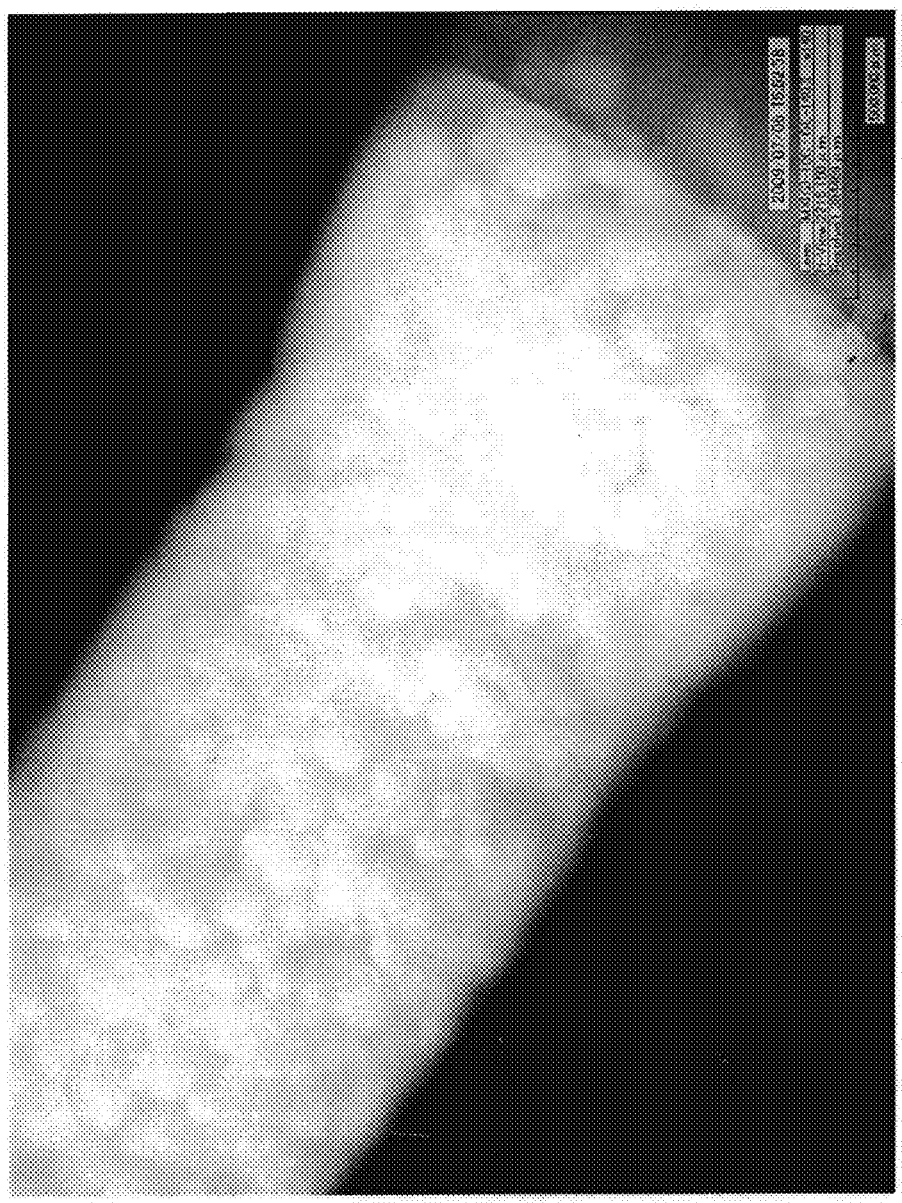
FIG. 6 illustrates a photomicrograph of a portion of an embodiment of a vent member.

Each of first section 82, including extending member 83 and portion 84 thereof, and second section 86 can, for example, be formed of a porous material that provides for diffusion of gas (for example, oxygen) therethrough while preventing passage of electrolyte therethrough. In several embodiments, first section 82 and second section 86 were formed integrally or monolithically of such a porous material. Alternatively, first section 82 can, for example, be formed separately and attached to second section 86. Likewise, extending member 83 can, for example, be formed separately from portion 84 and attached thereto. However, care must be taken during attachment to ensure a diffusion pathway through vent member 80 remains. In several embodiments, vent member 20 was formed monolithically from PTFE particles that were molded to form a hydrophobic, porous structure. A photomicrograph of a portion of a vent member formed form molded particles of PTFE having a maximum particle size of approximately 100 μm is illustrated in FIG. 6.

Figure 7:
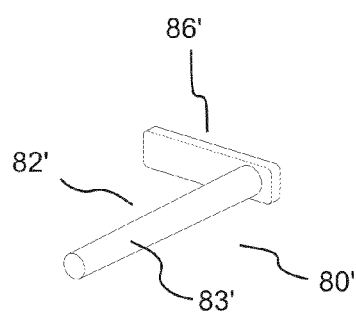
FIG. 7 illustrates a perspective view of another embodiment of a vent member.
Figure 5:
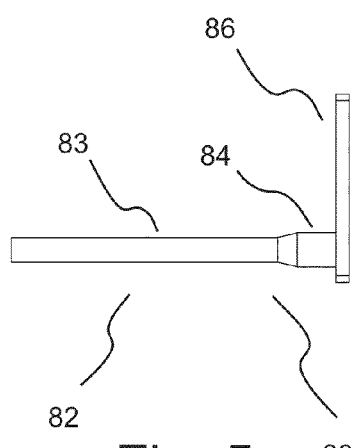
FIG. 5 illustrates another side view of the vent member of FIG. 1.

FIG. 7 illustrates another embodiment of a vent member 80' for use in connection with housing 20. In the embodiment illustrated in FIG. 7, a first section 82' includes an extending member 83' that has a tapered shape. That is, the diameter of extending member 83' is greater at a first end thereof connect to second section 86' than at a second or distal end thereof. The portion of extending member 83' in the vicinity of second section 86', passes through passage 24 in housing 20 when vent member 80' is in operative connection with housing 20. The diameter of extending member 83' at the junction of extending member 83' and second section 86' can, for example, be dimensioned to be slightly less than the diameter of passage 24. First section 82' and second section 86' can, for example, be formed monolithically as described above.

Figure 8A:
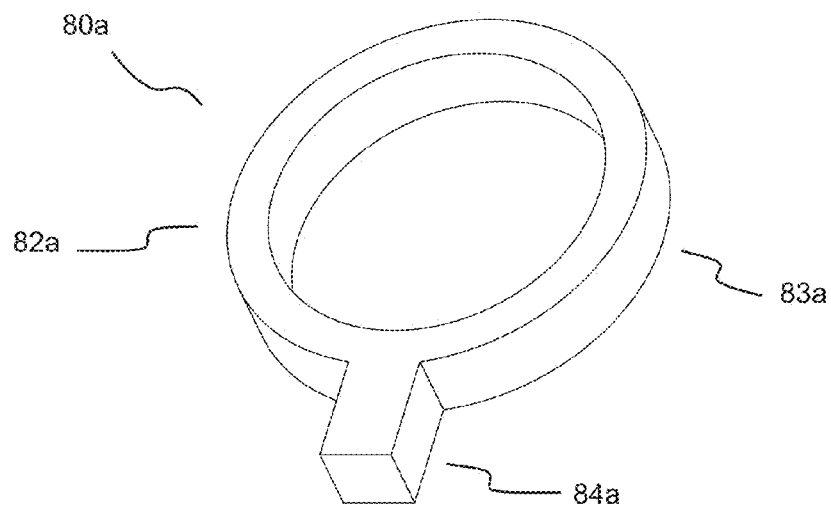
FIG. 8A illustrates another embodiment of a vent member.
Figure 8B:
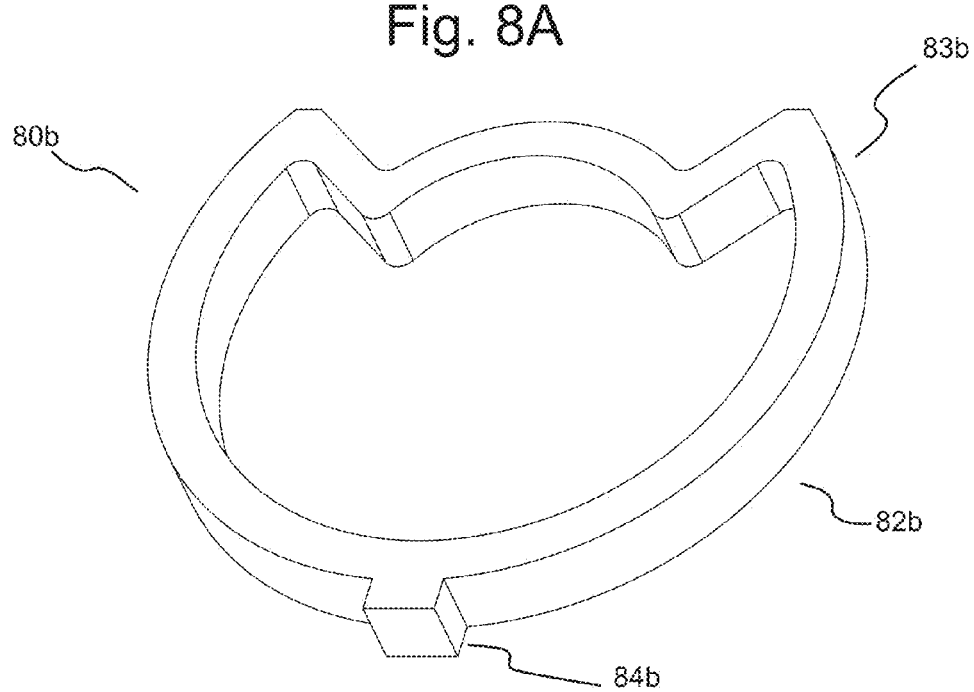
FIG. 8B illustrates another embodiment of a vent member.

FIGS. 8A and 8B illustrate alternative embodiments of vent members 80a and 80b, respectively, including at least a first section 82a and 82b, respectively, having extending members 83a and 83b which extend in a curvilinear manner through the interior of a sensor housing such as sensor housing 20. A portion or member 84a and 84b of vent members 80a and 80b, respectively, extends through a passage in the sensor housing to vent gas from the interior of the sensor housing to the exterior of the sensor housing. Vent members 80a and 80b can further include a second member or section (similar to or the same as second section 86 of vent member 80), which cooperates with the exterior of the housing to facilitate forming a (liquid) seal with the housing and to facilitate forming an adequate connection or attachment to the housing.

Figure 8C:
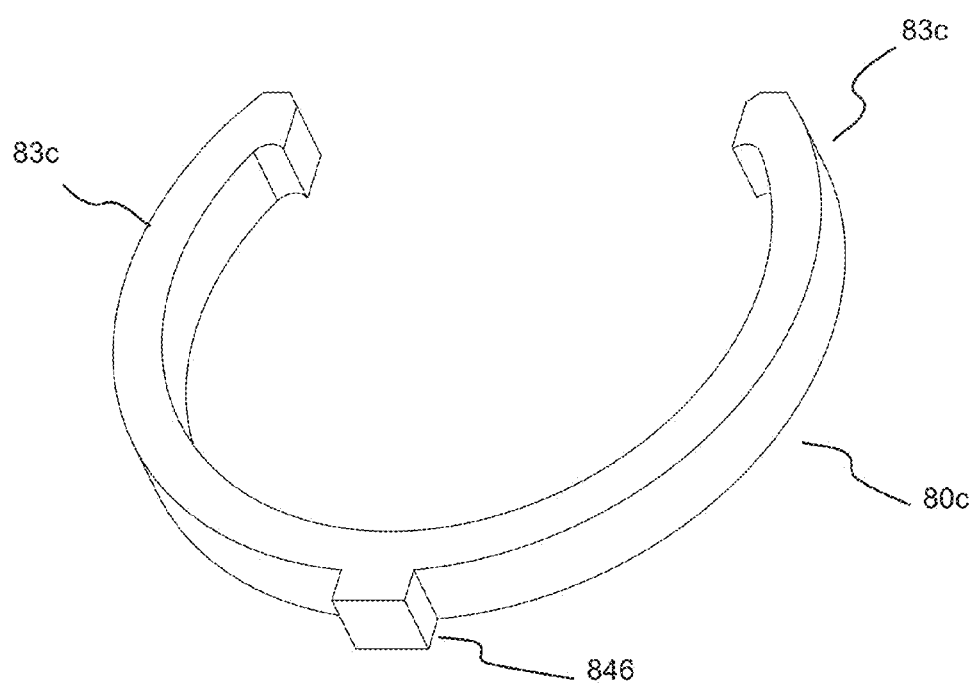
FIG. 8C illustrates another embodiment of a vent member.

In the embodiments of FIGS. 8A and 8B, extending members 83a and 83b form a closed loop. FIG. 8C illustrates an alternative embodiment of a vent members 80c including at least a first section 82c having a plurality of extending members 83c which extend in a curvilinear manner through the interior of a sensor housing such as sensor housing 20. A portion or member 84c of vent members 80c extends through a passage in the sensor housing to vent gas from the interior of the sensor housing to the exterior of the sensor housing.

The extending members illustrated in FIGS. 8A through 8C extend approximately laterally within, for example, sensor housing 20. However, the extending members hereof can extend longitudinally within such a housing. Moreover, one or more extending members (or one or more portions thereof) of the vent members hereof can, for example, have a branched structure to extend in one or more planes or directions.

Figure 9:
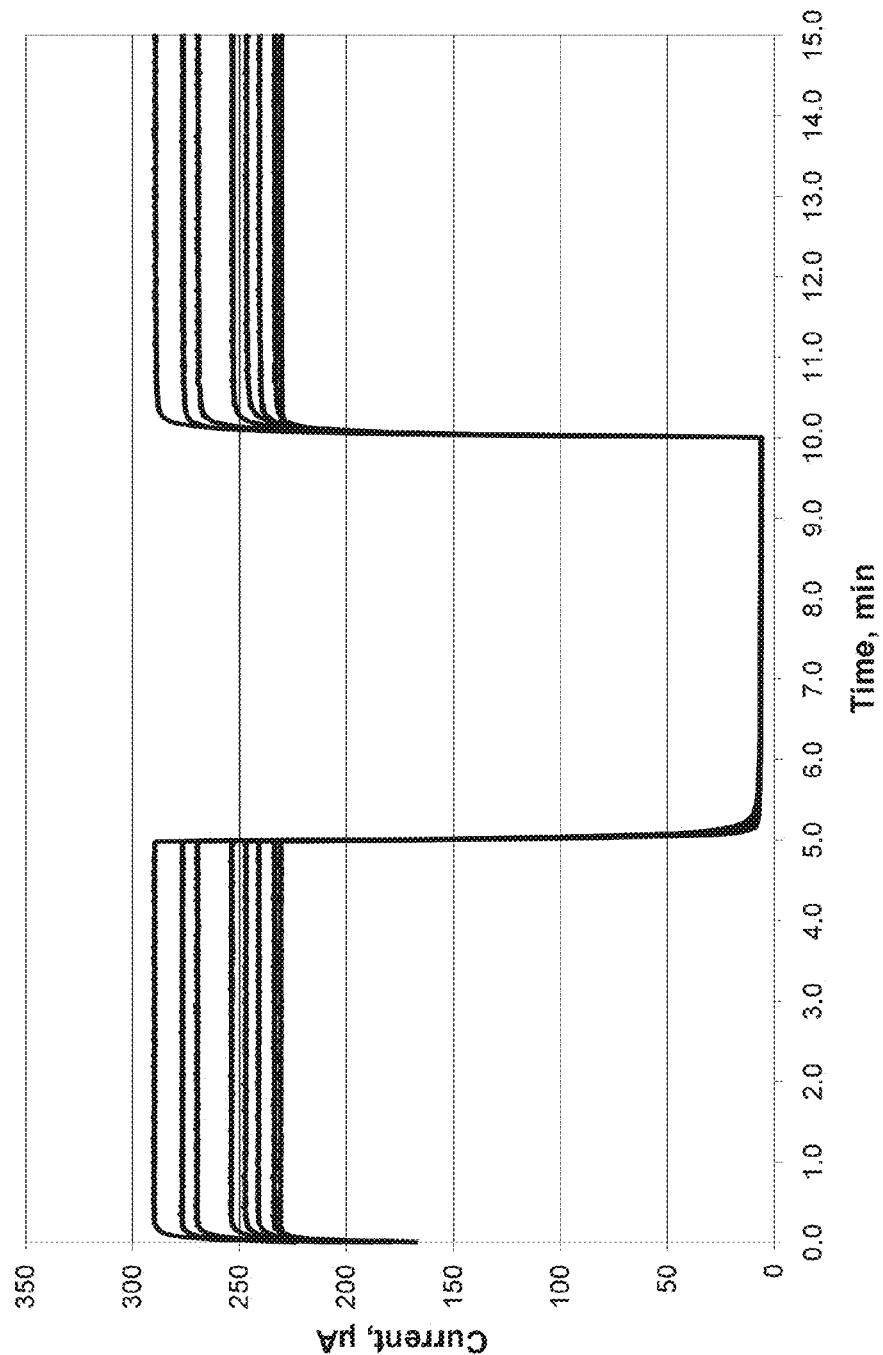
FIG. 9 illustrates the results of representative studies of one embodiment of an oxygen pump sensor including a vent member.

FIG. 9 illustrates results of representative studies for one embodiment of an oxygen pump sensor including a vent member 80 as described above. In the embodiment of the oxygen pump sensor of the studies, the working electrode, counter electrode and reference electrode each included platinum (Pt) black applied to one side of porous PTFE membranes. Each membrane served as a supporting structure, and, in the case of the working electrode, together with the Pt black, formed a gas diffusion electrode as known in the amperometric gas sensor arts. The working electrode was held at a potential of −600 mV, with respect to the reference electrode by an external potentiostat circuit.

FIG. 9 illustrates results typical of studies wherein sensors were subjected to a flow of air and a flow of nitrogen ($N_2$) (that is, gas having zero vol-% oxygen). In the experiments, air (including 20.8 vol-% $O_2$) was applied to the sensor at a flow rate of approximately 250 mL/min. At the 5 min mark in FIG. 9, the flow was suddenly switched to $N_2$, (that is, gas with 0.0 vol-% $O_2$). At the 10 min mark in FIG. 9, the flow stream was suddenly switched back to air (20.8 vol-% $O_2$ content). Table 1 sets forth typical performance characteristics of such sensors.

TABLE 1

|  | mean | std dev |
|---|---|---|
| Sensitivity, μA/vol-% $O_2$: | 12.0 | 1.0 |
| Corrected Ambient Output, μA: | 249 | 21 |
| Maximum Ambient Output, μA: | 255 | 21 |
| $N_2$ Baseline, μA: | 6 | 0 |
| $T_{90}$, down, sec: | 7.5 | 1.2 |
| $T_{90}$, up, sec: | 7.4 | 1.2 |
| RMS Noise, μA: | 0.72 | 0.33 |

The porous vent members of the sensors studied operated efficiently to vent gas from the sensors. Sensors without efficient gas venting would have failed over the duration of the studies performed.

The porous vent members can be used in connection with generally any container or housing (for example, in sensors, batteries etc) from which a gas must be vented (from the interior of the container/housing to the exterior thereof). As described above, the interior of the container or housing can include a liquid (such as an electrolyte) wherein the vent member resists or prevents flow of the liquid from the interior of the container to the exterior thereof but provides a diffusion path to vent gas.

The foregoing description and accompanying drawings set forth embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A sensor, comprising:
    a housing;
    at least two electrodes within the housing,
    an electrolyte within an interior volume of the housing, the electrolyte providing ionic conductivity between the electrodes; and
    a vent member comprising a first section comprising a portion extending through a passage in the housing and at least one extending member that extends from the first section through at least a portion of the interior volume of the housing so that the electrolyte does not wet an entirety of a surface of the at least one extending member that is in contact with the interior volume and the at least one extending member is in contact with a volume of gas within the interior volume of the housing and exterior to the at least one extending member regardless of the orientation of the housing, the portion extending through the passage in the housing and the at least one extending member of the first section being porous so that gas can diffuse through the first section from the interior of the housing to an exterior of the housing via the vent member.

2. The sensor of claim 1 wherein the vent member resists flow of electrolyte therethrough.

3. The sensor of claim 1 wherein the vent member further comprises a second section connected to the portion extending through the passage, the second section being porous and being attached to an exterior surface of the housing.

4. The sensor of claim 3 wherein the second section extends beyond the perimeter of the passage to cover the passage.

5. The sensor of claim 4 wherein the second section extends at an angle to the portion extending through the passage.

6. The sensor of claim 5 wherein the second section extends generally perpendicularly to the portion extending through the passage.

7. The sensor of claim 5 wherein the first section and the second section are formed monolithically from individual particles of polymeric material.

8. The sensor of claim 7 wherein at least a portion of the individual particles comprise polytetrafluoroethylene.

9. The sensor of claim 4 wherein the first section and the second section are formed monolithically from individual particles of polymeric material to provide a gas diffusion pathway therethrough.

10. The sensor of claim 1 wherein the at least one extending member is molded from individual particles of polymeric material.

11. The sensor of claim 10 wherein the at least one extending member of the vent member is hydrophobic, oleophobic or multiphobic.

12. The sensor of claim 1 wherein the first section is formed monolithically from individual particles of polymeric material to provide a gas diffusion pathway therethrough.

13. The sensor of claim 1 wherein at least one of the two electrodes is a working electrode adapted to reduce oxygen to an oxide ion and the sensor is adapted to sense oxygen.

14. A method of venting gas from an interior of a sensor comprising a housing, at least two electrodes within the housing and an electrolyte within an interior volume of the housing, the electrolyte providing ionic conductivity between the electrodes, comprising:
    providing a vent member comprising a first section comprising a portion extending through a passage in the housing and at least one extending member connected to the portion extending through the passage that extends through at least a portion of the interior of the housing so that the electrolyte does not wet an entirety of a surface of the at least one extending member that is in contact with the interior volume and the at least one extending member is in contact with a volume of gas within the interior volume of the housing and exterior to the at least one extending member regardless of the orientation of the housing, the portion extending through the passage in the housing and the at least one extending member of the first section being porous so that gas can diffuse through the first section from the interior of the housing to an exterior of the housing through the vent member.

15. A container for a liquid, comprising:
a housing comprising an interior volume for holding the liquid; and
a vent member comprising a first section comprising a portion extending through a passage in the housing and at least one extending member that extends through at least a portion of the interior of the housing so that the liquid does not wet an entirety of a surface of the at least one extending member that is in contact with the interior volume and the at least one extending member is in contact with a volume of gas within the interior volume of the housing and exterior to the at least one extending member regardless of the orientation of the housing, the portion extending through the passage in the housing and the at least one extending member of the first section being porous so that gas can diffuse through the first section from the interior of the housing to an exterior of the housing.

16. The container of claim 15 wherein the first section resists flow of liquid therethrough.

17. The container of claim 15 wherein the vent member further comprises a second section in connection with the portion extending through the passage, the second section being porous and being attached to an exterior surface of the housing.

18. The container of claim 17 wherein the second section extends at an angle to the portion extending through the passage.

19. The container of claim 18 wherein the first section and the second section are formed monolithically from individual particles of polymeric material.

20. The container of claim 15 wherein the at least one extending member is hydrophobic, oleophobic or multiphobic.

21. The container of claim 20 wherein the liquid comprises an electrolyte.

* * * * *